(12) United States Patent
Wang et al.

(10) Patent No.: US 11,099,184 B2
(45) Date of Patent: Aug. 24, 2021

(54) PROTEIN SENSOR AND MANUFACTURING METHOD THEREOF

(71) Applicant: National Taiwan University of Science and Technology, Taipei (TW)

(72) Inventors: Fu-Ming Wang, Taipei (TW); Yu-Lin Kuo, Taipei (TW); Wei-Ling Chen, Taipei (TW); Xing-Chun Wang, Taipei (TW); Chiou-Chung Yuan, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 0 days.

(21) Appl. No.: 16/879,790

(22) Filed: May 21, 2020

(65) Prior Publication Data

US 2021/0148901 A1    May 20, 2021

(30) Foreign Application Priority Data

Nov. 19, 2019   (TW) .................................. 108141910

(51) Int. Cl.
*G01N 33/543* (2006.01)
*G01N 33/574* (2006.01)

(52) U.S. Cl.
CPC ..... *G01N 33/5438* (2013.01); *G01N 33/5748* (2013.01)

(58) Field of Classification Search
None
See application file for complete search history.

(56) References Cited

U.S. PATENT DOCUMENTS 9,689,801 B2    6/2017  Kho et al.
2016/0319092 A1*  11/2016  Paulussen .............. B01D 65/08

FOREIGN PATENT DOCUMENTS

| CN | 102839534 A | * | 12/2012 |
| CN | 104931693 |   | 9/2015 |
| TW | M476999 |   | 4/2014 |
| TW | 201514861 |   | 4/2015 |
| TW | 201819918 |   | 6/2018 |

OTHER PUBLICATIONS

Srivastava et al., Electrophoretically deposited reduced graphene oxide platform for food toxin detection, 2013, Nanoscale, 3043-3051 (Year: 2013).*

Lee et al., Atmospheric pressure plasma treatment on graphene grown by chemical vapor deposition, Feb. 2015, Current Applied Physics, 563-568 (Year: 2015).*

Liang et al., Investigation of Reagent Delivery Formats in a Multivalent Malaria Sandwich Immunoassay and Implications for Assay Performance, Feb. 2016, Analytical Chemistry, 2311-2320 (Year: 2016).*

Desmet et al. On the effects of atmospheric-pressure microplasma array treatment on polymer and biological materials RSC Adv. 2013 3:13437-13445 (Year: 2013).*

Prysiazhnyi et al. Aging of plasma-activated copper and gold surface and its hydrophilic recovery after water immersion Thin Solid Films 2014 vol. 550: 373-380 (Year: 2014).*

Xiang Ren, et al., "Ultrasensitive immunoassay for CA125 detection using acid site com-pound as signal and enhancer", Talanta 144, Jul. 2, 2015, pp. 535-541.

K. Brince Paul, et al., "One step biofunctionalized electrospun multiwalled carbon nanotubes embedded zinc oxide nanowire interface for highly sensitive detection of carcinoma antigen-125", Biosensors and Bioelectronics 88, Aug. 2016, pp. 144-152.

Yun Zheng, et al., "A nanocomposite containing Prussian Blue, platinum nanoparticles and polyaniline for multi-amplification of the signal of voltammetric immunosensors: highly sensitive detection of carcinoma antigen 125", Microchim Acta 184, Aug. 24, 2017, pp. 4269-4277.

Subramanian Viswanathana, et al., "Molecular imprinted nanoelectrodes for ultra sensitive detection of ovarian cancer marker", Biosensors and Bioelectronics 33, Jan. 5, 2012, pp. 179-183.

Gisane Gasparotto, et al., "Electrochemical immunosensor based on ZnO nanorods-Au nanoparticles nanohybrids for ovarian cancer antigen CA-125 detection", Materials Science and Engineering C 76, Feb. 10, 2017,pp. 1240-1247.

M. Johari-Ahar, et al., "An ultra-sensitive impedimetric immunosensor for detection of the serum oncomarker CA-125 in ovarian cancer patients", Nanoscale 7, Jan. 17, 2015, pp. 3768-3779.

\* cited by examiner

*Primary Examiner* — Changhwa J Cheu
(74) *Attorney, Agent, or Firm* — JCIPRNET

(57) ABSTRACT

A manufacturing method of a protein sensor includes the following steps. A hydrophobic material is provided and the hydrophobic material has a surface. An atmospheric pressure plasma process is performed to form a hydrophilic functional group on the surface of the hydrophobic material. A first antibody is immobilized on the surface of the hydrophobic material by the hydrophilic functional group. A mixed solution is prepared. The mixed solution includes a second antibody and an analyte, and the second antibody binds to the analyte. The mixed solution is reacted with the first antibody immobilized on the surface of the hydrophobic material to bind the first antibody to the analyte. Furthermore, a protein sensor manufactured by the above-described manufacturing method of the protein sensor is also provided.

8 Claims, 8 Drawing Sheets

PROTEIN SENSOR AND MANUFACTURING METHOD THEREOF

CROSS-REFERENCE TO RELATED APPLICATION

This application claims the priority benefit of Taiwan patent application serial no. 108141910, filed on Nov. 19, 2019. The entirety of the above-mentioned patent application is hereby incorporated by reference here and made a part of this specification.

BACKGROUND

Technical Field

The disclosure relates to a sensor and a manufacturing method thereof, in particular, to a protein sensor and a manufacturing method thereof.

Description of Related Art

Clinical research results show that the current ovarian cancer symptoms are extremely difficult to detect and diagnose in the early stage, and the ovarian cancer is also a cancer of poor predictability. Among the patients suffering from the ovarian cancer, about 70% or above have been found to be in stage 3 or 4 upon detection of the ovarian cancer, so how to develop a cancer analyzer for early detection is very important.

On the other hand, at the present, the tracking of the ovarian cancer symptoms needs to rely on an image to find out a tumor location, or needs to detect an ovarian cancer tumor index CA125 by blood drawing to serve as a determination basis. In clinical analysis, an analysis index of CA125 at 35 U/mL or below would usually not be determined as abnormal. However, in a certain proportion of patients, it has been found that CA125 may still contribute to the diagnosis of recurrence even under a fluctuation behavior at an extremely low index (less than 5 U/mL). However, the signal fluctuation range of traditional immunoassay, such as enzyme immunoassay (EIA) and radioimmunoassay (RIA), is too wide, and it is not easy to identify the scientific significance.

SUMMARY

The invention provides a protein sensor configured to identify types and quantities of proteins and having a relatively low detection limit and relatively good sensitivity.

The invention provides a manufacturing method of the protein sensor, which is configured to manufacture the foregoing protein sensor.

The manufacturing method of the protein sensor of the invention includes the following steps: firstly, providing a hydrophobic material, where the hydrophobic material has a surface; secondly, performing an atmospheric pressure plasma process to form a hydrophilic functional group on the surface of the hydrophobic material; then, immobilizing a first antibody on the surface of the hydrophobic material by the hydrophilic functional group; later, preparing a mixed solution where the mixed solution includes a second antibody and an analyte, and the second antibody binds to the analyte; and finally, reacting the mixed solution with the first antibody immobilized on the surface of the hydrophobic material to bind the first antibody to the analyte.

In an embodiment of the invention, the hydrophobic material includes graphite, graphene, or a gold sheet.

In an embodiment of the invention, the hydrophilic functional group includes a carboxyl group, a hydroxyl group, or a combination thereof.

In an embodiment of the invention, the step of immobilizing the first antibody to the surface of the hydrophobic material by the hydrophilic functional group includes: bonding an amino acid of the first antibody to the hydrophilic functional group on the surface of the hydrophobic material.

In an embodiment of the invention, the atmospheric pressure plasma process is a wet atmospheric pressure plasma modification method. The wet atmospheric pressure plasma modification method includes the following steps: firstly, dispersing the hydrophobic material in deionized water; and next, applying an atmospheric pressure plasma with a current of 10 mA to the surface of the hydrophobic material for 3 min.

In an embodiment of the invention, the atmospheric pressure plasma process includes a dry atmospheric pressure plasma modification method. The dry atmospheric pressure plasma modification method includes the following step: applying an atmospheric pressure plasma with a power of 500 W and a frequency of 32 Hz to the surface of the hydrophobic material.

In an embodiment of the invention, a source of the analyte includes a cell extract or serum.

In an embodiment of the invention, the analyte is a tumor marker CA125.

The protein sensor of the invention is manufactured according to the above-mentioned manufacturing method of the protein sensor.

In an embodiment of the invention, the protein sensor has a lowest detection limit of $2.7 \times 10^{-2}$ ng/mL to 3.2 ng/mL.

Based on the above, in the protein sensor and the manufacturing method thereof provided by the present embodiment, the hydrophilic functional group is formed on the surface of the hydrophobic material by using the atmospheric pressure plasma process, so that the first antibody may be immobilized on the surface of the hydrophobic material through the hydrophilic functional group. Then, the first antibody is used to identify and bind to the analyte that binds to the second antibody, thereby forming the protein sensor of the present embodiment. Then, detection is performed electrochemically. In this way, the protein sensor of the present embodiment may be used to identify the types and quantities of proteins, and has a relatively low detection limit and relatively good sensitivity.

DESCRIPTION OF THE EMBODIMENTS

Figure 1:
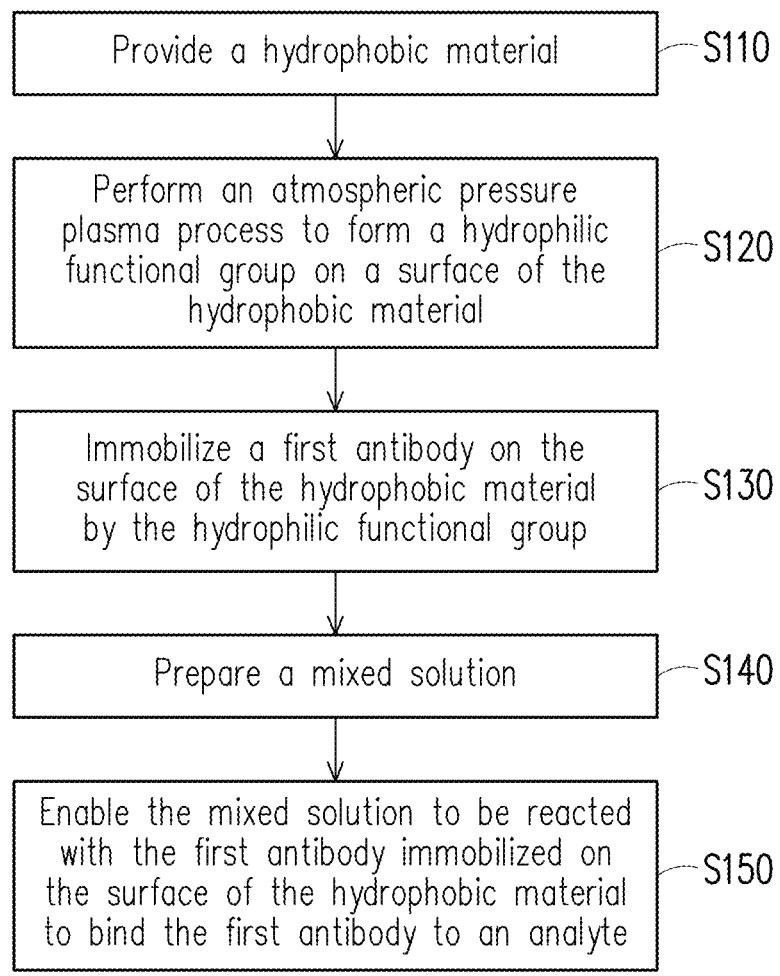
FIG. 1 is a flow diagram of a manufacturing method of a protein sensor according to an embodiment of the invention.

FIG. 1 is a flow diagram of a manufacturing method of a protein sensor according to an embodiment of the invention. Referring to FIG. 1, firstly, at step S110, a hydrophobic material is provided. In the present embodiment, the hydrophobic material may include graphite, graphene, reduced graphene oxide, or a gold sheet, but it is not limited to this.

Secondly, at step S120, an atmospheric pressure plasma process is performed to form a hydrophilic functional group on a surface of the hydrophobic material. In the present embodiment, the atmospheric pressure plasma process may be a wet atmospheric pressure plasma modification method or a dry atmospheric pressure plasma modification method. The hydrophilic functional group may include a carboxyl group, a hydroxyl group, or a combination of the carboxyl group and the hydroxyl group, but it is not limited to this. Specifically, in steps of the wet atmospheric pressure plasma modification method of the present embodiment, the graphite or graphene is firstly dispersed in deionized water, and then an atmospheric pressure plasma with a current of 10 mA is applied to a surface of the graphite or graphene to act for 3 min, so that the hydrophilic functional group including the carboxyl group, the hydroxyl group, or the combination of the carboxyl group and the hydroxyl group may be formed on the surface of the graphite or graphene. In addition, in steps of the dry atmospheric pressure plasma modification method of the present embodiment, after an atmospheric pressure plasma with a power of 500 W and a frequency of 32 Hz is applied to a surface of the gold sheet, the hydrophilic functional group including the carboxyl group, the hydroxyl group, or the combination of the carboxyl group and the hydroxyl group may be formed on the surface of the gold sheet.

Later, at step S130, a first antibody is immobilized on the surface of the hydrophobic material by the hydrophilic functional group. In the present embodiment, an amino acid of the first antibody may be directly reacted with and bonded to the carboxyl group or hydroxyl group on the surface of the graphite, the graphene, or the gold sheet through a chemical reaction, so that the first antibody may be immobilized to the surface of the graphite, the graphene, or the gold sheet, and is not easy to fall off.

Then, at step S140, a mixed solution is prepared. In the present embodiment, the mixed solution at least includes a second antibody and an analyte. The second antibody may identify and bind to the analyte. In the present embodiment, a source of the analyte is, for example, a protein in a cell extract or serum in blood, but it is not limited to this. The analyte is, for example, a tumor marker CA125 or other proteins or peptides to be detected, but it is not limited to this.

Finally, at step S150, the mixed solution is reacted with the first antibody immobilized on the surface of the hydrophobic material to bind the first antibody to the analyte. Specifically, in the present embodiment, the analyte binding to the second antibody may be identified by and bind to the first antibody, so that the analyte binding to the second antibody may be immobilized to the surface of the graphite, the graphene, or the gold sheet through the first antibody. In other words, the first antibody and the second antibody may simultaneously identify and bind to different positions on the analyte, so that the analyte is located between the first antibody and the second antibody. At this time, the protein sensor of the present embodiment has been manufactured. In the present embodiment, the protein sensor has a lowest detection limit of, for example, $2.7 \times 10^{-2}$ ng/mL to 3.2 ng/mL, but it is not limited to this.

Different embodiments will be exemplified to describe how to manufacture a protein sensor. However, these embodiments are exemplary, and the invention is not limited to this.

[Embodiment 1] Protein Sensor Manufactured by the Wet Atmospheric Pressure Plasma Modification Method FIG. 2A to FIG. 2E are schematic diagrams of a protein sensor manufactured by a wet atmospheric pressure plasma modification method in an embodiment of the invention.

Figure 2A:
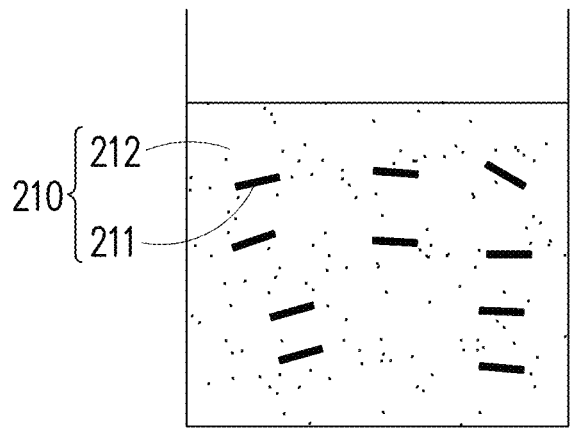
FIG. 2A to FIG. 2E are schematic diagrams of a protein sensor manufactured by a wet atmospheric pressure plasma modification method in an embodiment of the invention.
Figure 2B:
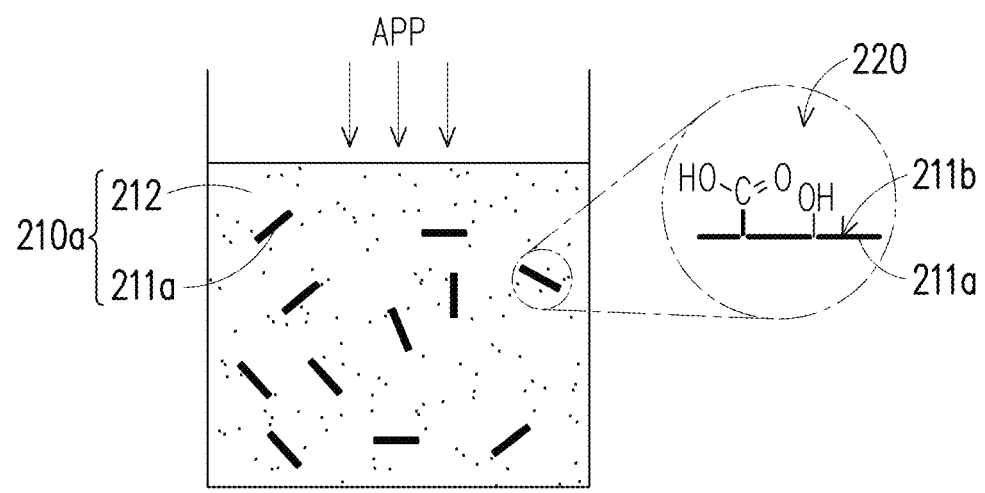

Referring to FIG. 2A at first, 0.13 g of reduced graphene oxide 211 was dissolved in 13 mL of deionized water 212 to obtain a reduced graphene oxide aqueous solution 210. Next, referring to FIG. 2B, the reduced graphene oxide 211 in the reduced graphene oxide aqueous solution 210 was subjected to surface modification by, for example, an atmospheric pressure plasma APP at 10 milliamperes (mA). After the action lasted for 3 min, a surface 211b of the reduced graphene oxide 211a, modified by the atmospheric pressure plasma, in the reduced graphene oxide aqueous solution 210a modified by the atmospheric pressure plasma at least had a hydrophilic functional group 220 such as a carboxyl group, a hydroxyl group, or a combination of the carboxyl group and the hydroxyl group.

Figure 2C:
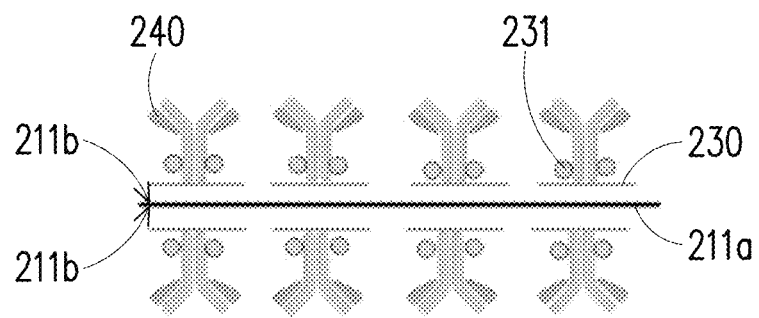

Referring to FIG. 2C, 1 mL of the reduced graphene oxide aqueous solution 210a modified by the atmospheric pressure plasma was taken, and 10 mL of thionine 230 at a concentration of 1 mM and 10 mL of phosphate buffered saline (PBS) at a concentration of 0.1 mM were added, and were mixed and reacted at 37° C. and a rotating speed of 300 rpm for 48 h, so as to enable the thionine 230 to be connected to the surface 211b of the modified reduced graphene oxide 211a. After 48 h, 10 mL of PBS at a concentration of 0.1 M and 10 mL of glutaraldehyde 231 at a concentration of 2.5 wt % were added, and were mixed and reacted at room temperature at the rotating speed of 300 rpm for 1 h. Then, 2 µL of a first antibody 240 was added, and was mixed and reacted at 4° C. at a rotating speed of 2 rpm for 24 h to obtain a mixed solution A.

Specifically, in the present embodiment, in the mixed solution A, the thionine 230 may be connected to the surface 211b of the modified reduced graphene oxide 211a, and a main acting force between the thionine 230 and the modified reduced graphene oxide 211a was, for example, a π-π acting force. In the present embodiment, the first antibody 240 was, for example, directly bonded to the thionine 230 by means of a condensation reaction, but it is not limited to this. In some embodiments, an amino acid of the first antibody may also be directly bonded to the hydrophilic functional group (not shown) by means of a condensation reaction. In the present embodiment, a carboxyl group of the first antibody 240 may be subjected to the condensation reaction with an amine group of the thionine 230 to bind the first antibody 240 to the thionine 230. In the present embodiment, the glutaraldehyde 231 may be connected to the first antibody 240 to make it easier for the first antibody 240 to be bonded to the hydrophilic functional group 220.

In addition, in some embodiments, the aforementioned thionine 230 may also be substituted with toluene blue, and the aforementioned glutaraldehyde 231 may also be substituted with 1-ethyl-3-(3-dimethylaminopropyl) carbodiimide (EDC), N-hydroxysuccinimide (NHS) or hexamethylene diamine.

Figure 2D:
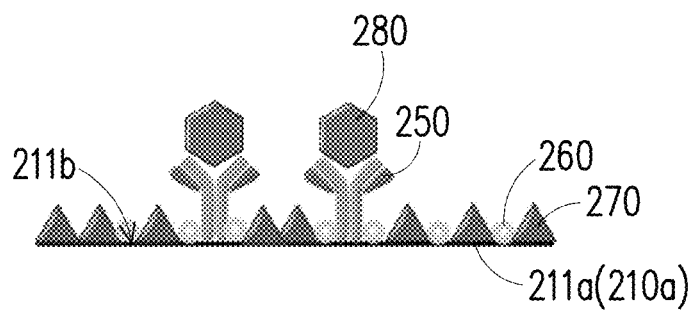

Referring to FIG. 2D, a mixed solution B was prepared: 1 mL of the reduced graphene oxide aqueous solution 210a modified by the atmospheric pressure plasma was taken, and 10 mL of PBS at a concentration of 0.1 wt % and 10 µL of a second antibody 250 were added, and were mixed and reacted at the room temperature at the rotating speed of 300 rpm for 1 h. Then, 2 mL of an aqueous solution of gold nanoparticles 260 and 4 mL of bovine serum albumin (BSA) 270 at a concentration of 1 wt % were added, and were mixed and reacted at the room temperature at the rotating speed of 300 for 1 h. So far, the mixed solution B had been prepared.

Specifically, in the mixed solution B, the second antibody 250 was, for example, directly bonded to the hydrophilic functional group 220 on the surface 211b of the modified reduced graphene oxide 211a by means of the condensation reaction. The BSA was attached to the surface 211b of the modified reduced graphene oxide 211a to fill a gap, which was not grafted with the second antibody 250, on the surface 211b. The gold nanoparticles 260 were, for example, attached to the surface 211b of the modified reduced graphene oxide 211a by means of adsorption to increase a conductivity of a protein sensor 200. In addition, in some embodiments, the aforementioned gold nanoparticles (AuNPs) 260 may also be substituted with horseradish peroxidase (HRP) or silver nanoparticles (AgNPs).

Continuously referring to FIG. 2D, the prepared mixed solution B was subpackaged into 6 beakers, and each of the beakers contains 1.5 mL of the mixed solution B. Next, 2 µL of an antigen 280 at different concentrations was added into each beaker, and was mixed and reacted at the room temperature at the rotating speed of 300 rpm for 1 h to obtain a mixed solution C.

Figure 2E:
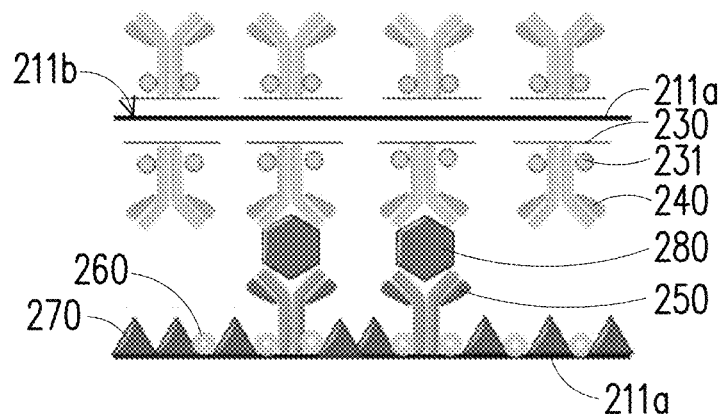

Referring to FIG. 2E, after the reaction was completed, 6 mL of the mixed solution A was added into the mixed solution C, so that the mixed solution A and the mixed solution C were mixed and reacted at the room temperature at the rotating speed of 300 rpm for 1 h. So far, the protein sensor 200 of the present embodiment had been manufactured.

In the present embodiment, the overall reactivity of the protein sensor 200 may be improved by using the thionine 230. For example, the thionine 230 may contribute to the formation of a second antibody 250/antigen 280/first antibody 240 structure. The thionine 230 may also enable the protein sensor 200 to make electron transport in an electrochemical reaction smooth during the subsequent electrochemical reaction. In addition, in the present embodiment, the thionine 230 may be used as a basis for determining an electrochemical redox reaction current.

Figure 3:
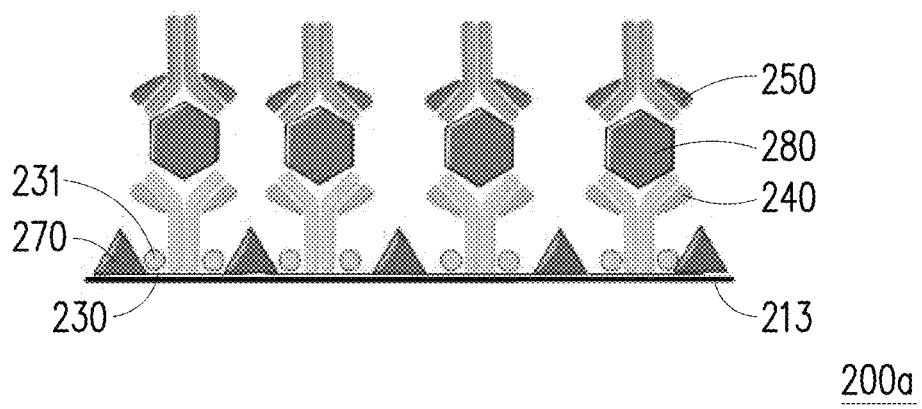
FIG. 3 is a schematic diagram of a protein sensor manufactured by a dry atmospheric pressure plasma modification method in an embodiment of the invention.

[Embodiment 2] Protein Sensor Manufactured by the Dry Atmospheric Pressure Plasma Modification Method FIG. 3 is a schematic diagram of a protein sensor manufactured by a dry atmospheric pressure plasma modification method in an embodiment of the invention.

2 µL of deionized water was dropped on a surface of gold on a wafer, and a water contact angle was measured. At this time, a value of the water contact angle was, for example, 70 to 80 degrees. Then, water was dried via suction by using lens paper, the wafer was immobilized to a platform deck by using a heat insulating tape, and the platform deck was placed on a conveying belt. A distance between the wafer and a pressure plasma spray head was adjusted until they were 0.5 cm apart. Then, an air exhaust system of the pressure plasma and an air dryer were turned on to enable an instrument to drain water. After it was confirmed that the water had been discharged, a drainage switch might be turned off, and parameters of a pressure plasma instrument were set: a target position of movement of the conveying belt was, for example, X=62.6 mm, Y=232.87 mm, Z=0 mm, but it was not limited to this. A moving speed of the conveying belt was, for example, dX=120 mm and dY=10 mm, but it was not limited to this.

Then, an atmospheric pressure plasma APP with a power of, for example, 500 W and a frequency of, for example, 32 Hz was used to perform surface modification on the gold on the wafer, so that the surface of the gold at least had a hydrophilic functional group such as a carboxyl group, a hydroxyl group, or a combination of the carboxyl group and the hydroxyl group. Next, on the wafer of the gold 213 modified by atmospheric pressure plasma, 2 µL of deionized water was dropped on the surface of the modified gold 213, and a water contact angle was measured. At this time, since the surface of the modified gold 213 had the hydrophilic functional group, water would be rapidly dispersed on the surface of the modified gold 213, so the water contact angle might not be measured.

A mixed solution A1 was prepared from: 60 µL of PBS, 30 µL of glutaraldehyde 231, 30 µL of thionine 230 (0.1 M), and 1 µL of the first antibody 240. Then, 15 µL of the prepared mixed solution A1 was dropped to the surface of the gold 213 modified by the atmospheric pressure plasma, and was left to stand at 4° C. and reacted for about 24 h. At this time, the thionine 230 may be connected to the surface of the modified gold 213, and a main acting force between the thionine 230 and the modified gold 213 was, for example, a π-π acting force. The thionine 230 may be used as a basis for subsequent electrochemical redox determination. The first antibody 240 was, for example, directly bonded to the thionine 230 by means of a condensation reaction. The glutaraldehyde 231 may be connected to the first antibody 240 to make it easier for the first antibody 240 to be bonded to the hydrophilic functional group.

A mixed solution B1 was prepared from: 60 µL of PBS, 20 µL of thionine 230 (0.1 M), and 3.38 µL of the second antibody 250. Then, 15 µL of the prepared mixed solution B1 was respectively added into microburettes, and then 2 µL of the antigen 280 at different concentrations was respectively added. Then, the microburettes were left to stand at 4° C., and reacted for about 1 h to obtain a mixed solution C1. At this time, the second antibody 250 may identify and bind to the antigen 280.

After the mixed solution A1 was reacted with the modified gold 213 for 24 h, liquid on the surface of the modified gold 213 was dried via suction by using the lens paper. Next, 15 µL of the mixed solution C1 was dropped to the surface of the modified gold 213 respectively, and was left to stand at 4° C. and reacted for about 1 h. After the reaction lasted for 1 h, liquid on the surface of the modified gold 213 was dried via suction by using the lens paper, and the wafer was inserted into a connection box. At this time, the antigen 280 binding to the second antibody 250 may be identified by and bind to the first antibody 240, so that the antigen 280 binding to the second antibody 250 may be immobilized on the surface of the modified gold 213 through the first antibody 240. So far, a protein sensor 200a of the present embodiment had been manufactured, as shown in FIG. 3.

In short, in the present embodiment, the atmospheric pressure plasma process (such as the wet atmospheric pressure plasma modification method or the dry atmospheric pressure plasma modification method) may be used to form the hydrophilic functional group (such as the carboxyl group, the hydroxyl group, or the combination of the carboxyl group and the hydroxyl group) on the surface of the hydrophobic material. Then, the first antibody may be used to identify and bind to the analyte that binds to the second antibody, thereby forming the protein sensor of the present embodiment. The first antibody may be directly bonded to the hydrophilic functional group in a chemical bonding manner, so that the first antibody may be immobilized on the hydrophobic material and may not be easy to fall off.

Different embodiments will be exemplified below to explain how to use the protein sensor manufactured above to detect an ovarian cancer tumor marker CA125. In the present embodiment, a source of the ovarian cancer tumor marker CA125 may be a commercial CA125 antigen, a cancer cell extract, or serum of a patient, but it is not limited to this. However, these embodiments are exemplary, and the invention is not limited to this.

Figure 4:
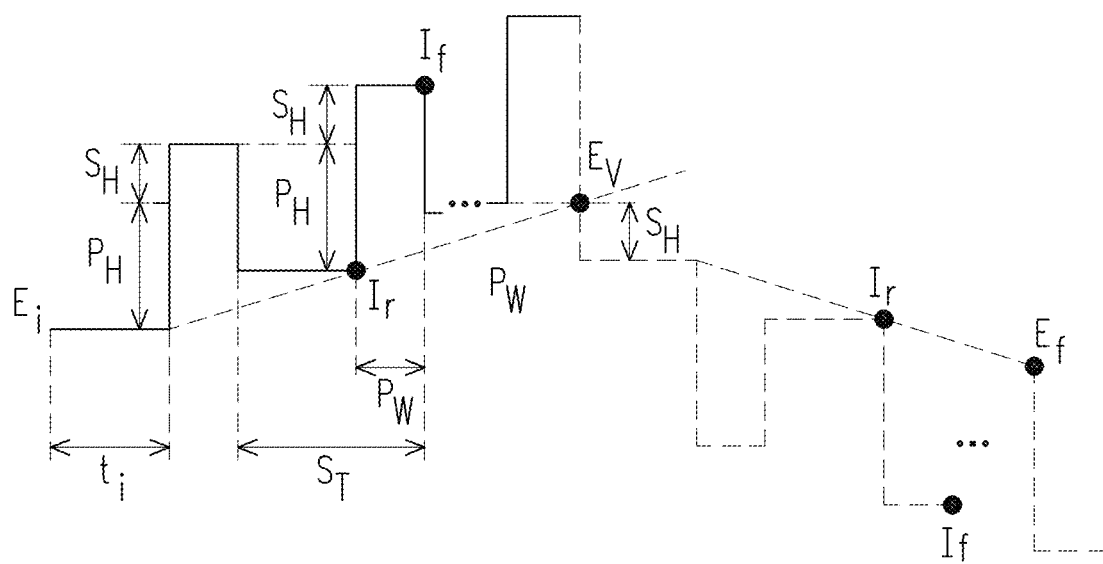
FIG. 4 is a schematic diagram of parameters of an electrochemical test performed on a protein sensor according to an embodiment of the invention.

FIG. 4 is a schematic diagram of parameters of an electrochemical test performed on a protein sensor according to an embodiment of the invention.

Referring to FIG. 4, the protein sensor of the present embodiment detects proteins in a unidirectional scanning manner by pulse voltammetry, and parameters of an electrochemical test are set as follows: an initial stable voltage value ($E_i$) is, for example, 0.35 V to 0.65 V; a voltage value ($E_v$) at the end of the experiment is, for example, -1 V to -1.5 V; a height of voltage pulse ($P_H$) is, for example, 20 mV to 100 mV; a time of voltage pulse ($P_W$) is, for example, 20 ms to 100 ms; a voltage ($S_H$) of a pulse voltage that changes in a positive/negative direction is, for example, -0.5 mV to -25 mV; and a pulse time+standing time ($S_T$) is, for example, 40 ms to 200 ms. $E_i$ and $E_v$ represent test intervals; $P_H$ represents a volt setting maintained at each stage; $P_W$ represents a time setting maintained at each stage; $S_H$ represents an increase or decrease setting of a volt at each stage; $S_T$ represents a total time of a pulse test at each stage; $I_f$ represents a forward current value of the test; $I_r$ represents a current value of a test change; $T_i$ represents a waiting test time; and $E_f$ represents a scan termination potential.

Figure 5A:
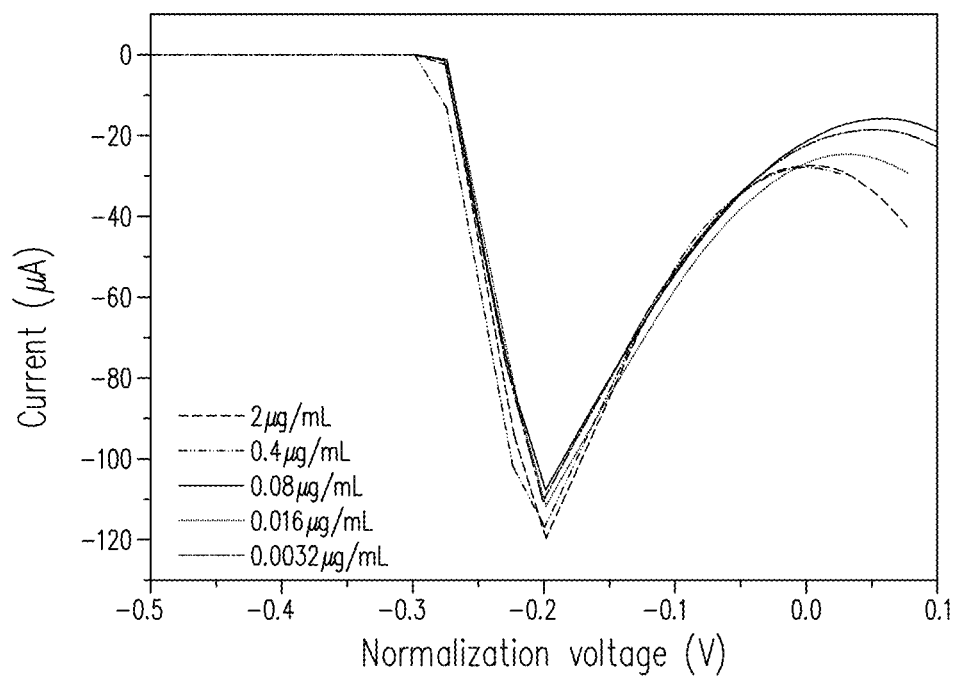
FIG. 5A is a result obtained by using a protein sensor of an embodiment of the invention to detect a commercial CA125 antigen.
Figure 5B:
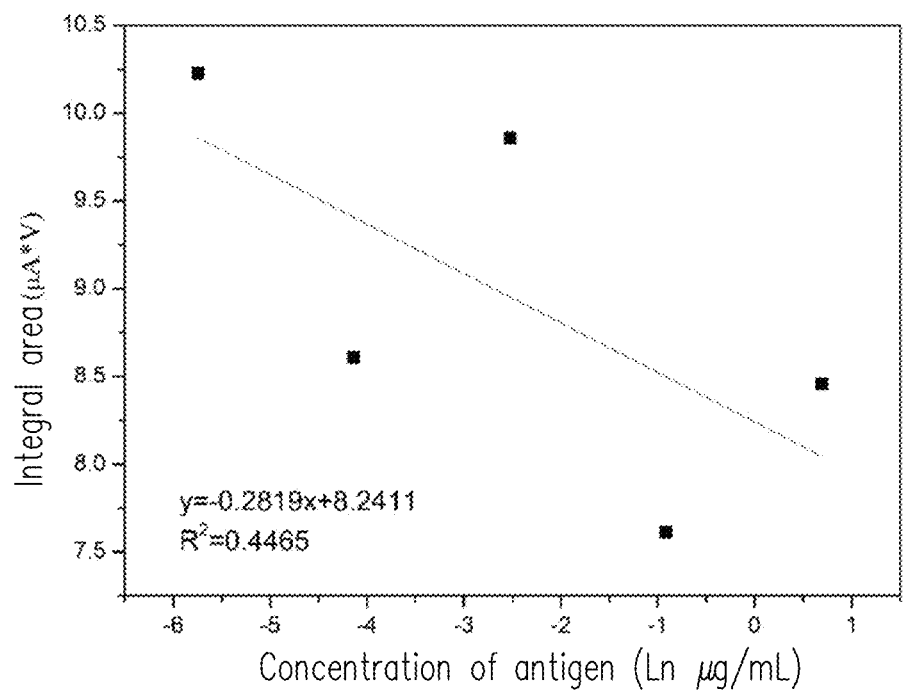
FIG. 5B is a relationship diagram between a protein concentration and an integral area in FIG. 5A.

[Embodiment 3] Detect Ovarian Cancer Tumor Marker CA125 by Using the Protein Sensor Manufactured by the Wet Atmospheric Pressure Plasma Modification Method FIG. 5A is a result obtained by using a protein sensor of an embodiment of the invention to detect a commercial CA125 antigen. FIG. 5B is a relationship diagram between a protein concentration and an integral area in FIG. 5A.

After 0.5 mL to 1 mL of hydrogen peroxide and 10 μL to 15 μL of Ag/AgCl were added into the protein sensor manufactured in Embodiment 1, uniform mixing was performed, and an electrochemical test was performed according to the parameters of FIG. 4.

Referring to FIG. 5A, commercial CA125 antigens at different concentrations were detected by using the protein sensor manufactured by the wet atmospheric pressure plasma modification method. The concentrations of the commercial CA125 antigens were 2, 0.4, 0.08, 0.016, and 0.0032 μg/mL respectively. The Y-axis shows reaction current (μA), and the X-axis shows a normalization voltage (V). It may be known from the results of FIG. 5A that as the concentrations of the commercial CA125 antigens increase, integral areas of corresponding electrochemically sensed signals are smaller. Next, referring to FIG. 5B, it illustrates the relationship diagram and a trend line of the concentrations of the commercial CA125 antigens vs. the integral areas according to the results of FIG. 5A. It may be known from the results of FIG. 5B that a formula of the trend line is y=-0.2819x+8.2411, and a correlation coefficient ($R^2$) is 0.4465. In addition, it may be known from the results of FIG. 5A and FIG. 5B that the lowest detection limit of the protein sensor is 3.2 ng/mL.

Figure 6A:
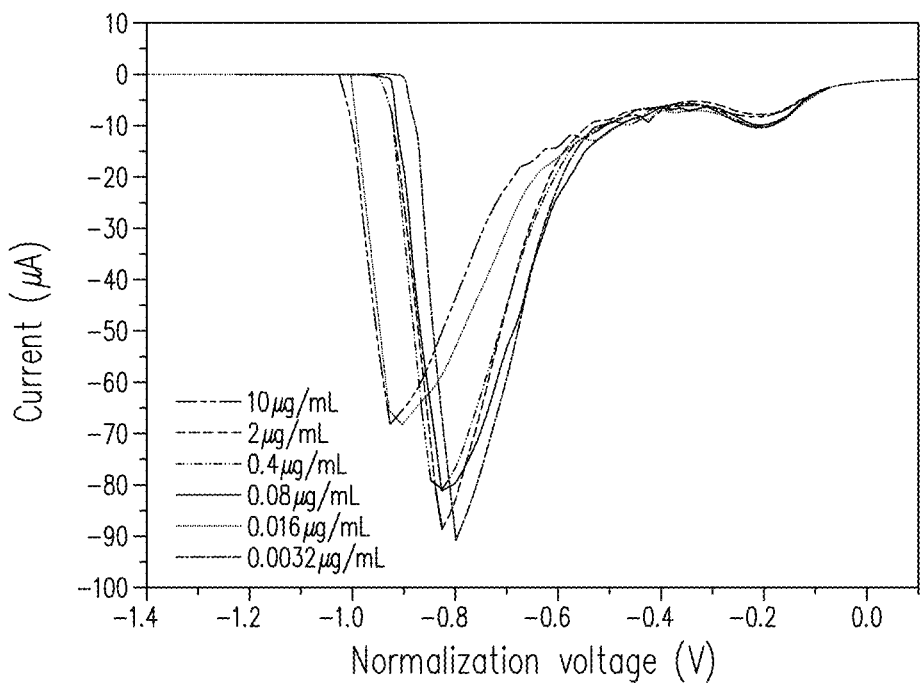
FIG. 6A and FIG. 6C are results obtained by using a protein sensor of another embodiment of the invention to detect a commercial CA125 antigen and serum of a patient.
Figure 6B:
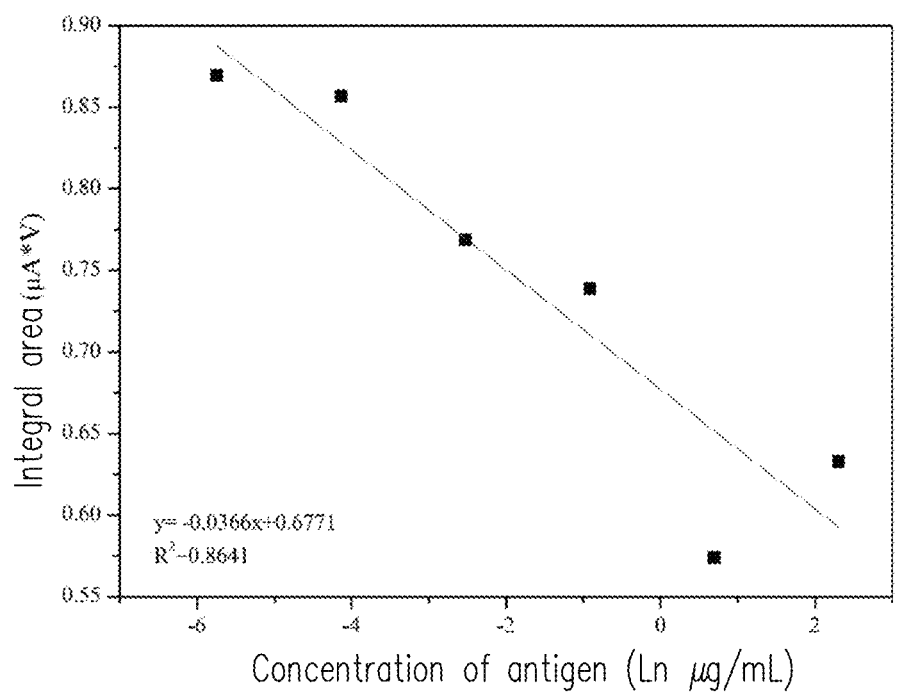
FIG. 6B and FIG. 6D respectively illustrate relationship diagrams between protein concentrations and integral areas in FIG. 6A and FIG. 6C.
Figure 6C:
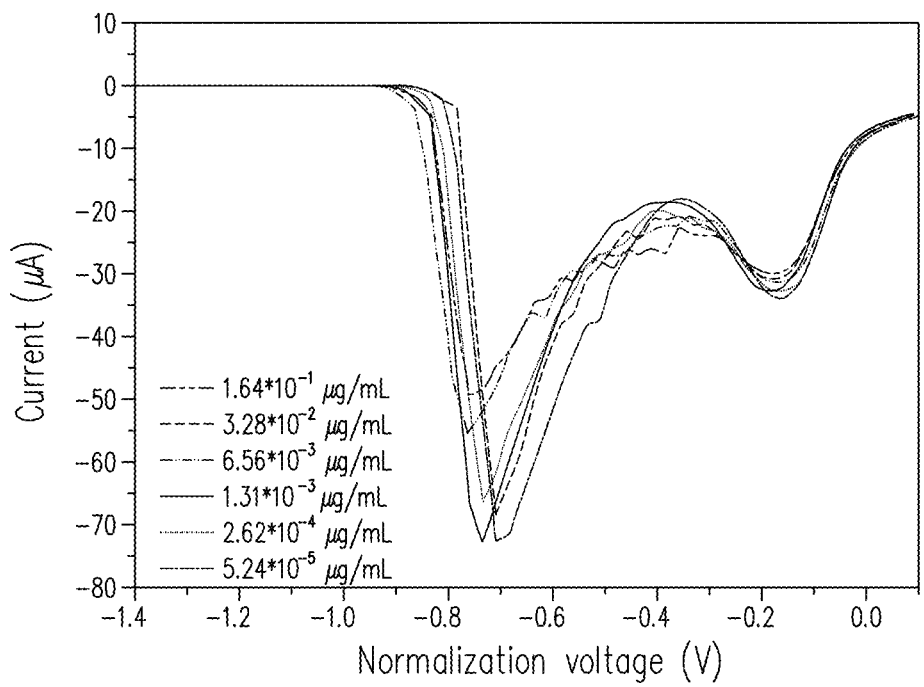
Figure 6D:
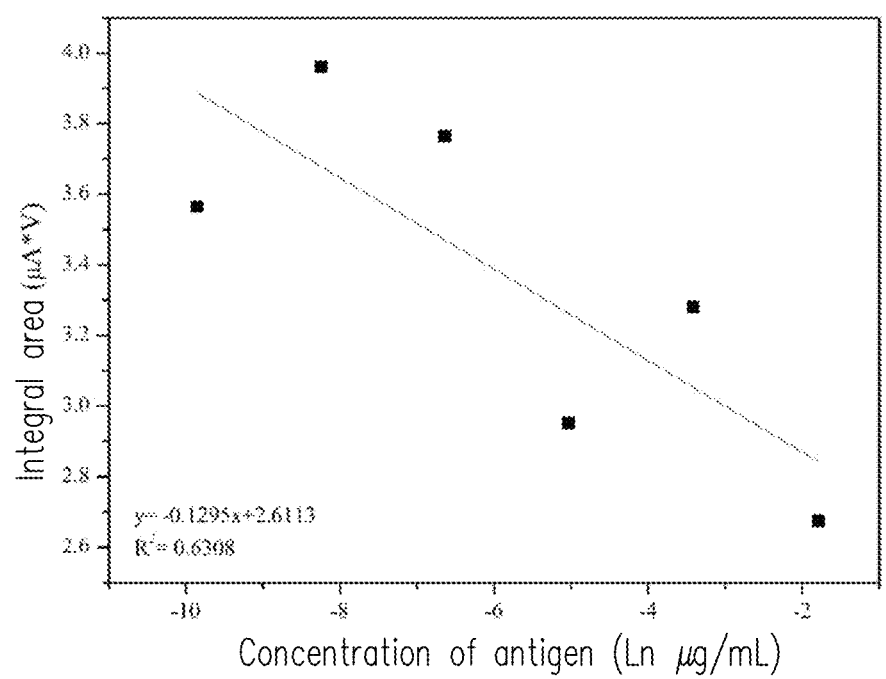

[Embodiment 4] Detect Ovarian Cancer Tumor Marker CA125 by Using the Protein Sensor Manufactured by the Dry Atmospheric Pressure Plasma Modification Method FIG. 6A and FIG. 6C are results obtained by using a protein sensor of another embodiment of the invention to detect a commercial CA125 antigen and serum of a patient. FIG. 6B and FIG. 6D respectively illustrate relationship diagrams between protein concentrations and integral areas in FIG. 6A and FIG. 6C.

185 μL of PBS and 15 μL of hydrogen peroxide were uniformly mixed, and then covered all electrodes on the protein sensor manufactured in Embodiment 3, so as to perform an electrochemical test according to the parameters of FIG. 4.

Referring to FIG. 6A, commercial CA125 antigens at different concentrations were detected by using the protein sensor manufactured by the dry atmospheric pressure plasma modification method. The concentrations of the commercial CA125 antigens were 10, 2, 0.4, 0.08, 0.016, and 0.0032 μg/mL respectively. The X-axis shows current (μA), and the Y-axis shows a normalization voltage (V). It may be known from the results of FIG. 6A that as the concentrations of the commercial CA125 antigens increase, integral areas of corresponding electrochemically sensed signals are smaller. Next, referring to FIG. 6B, it illustrates the relationship diagram and a trend line of the concentrations of the commercial CA125 antigens vs. the integral areas according to the results of FIG. 6A. It may be known from the results of FIG. 6B that a formula of the trend line is y=0.0366x+0.671, and a correlation coefficient ($R^2$) is 0.8641. In addition, it may be known from the results of FIG. 6A and FIG. 6B that the lowest detection limit of the protein sensor is 3.2 ng/mL.

Referring to FIG. 6C, the serum of the patient at different concentrations was detected by using the protein sensor manufactured by the dry atmospheric pressure plasma modification method. The concentrations of proteins in the serum of the patient were $1.64 \times 10^{-1}$, $3.28 \times 10^{-2}$, $6.56 \times 10^{-3}$, $1.31 \times 10^{-3}$, $2.62 \times 10^{-4}$, and $5.24 \times 10^{-5}$ μg/mL respectively. It may be known from the results of FIG. 6C that as the concentrations of the proteins in the serum of the patient increase, integral areas of corresponding electrochemically sensed signals are smaller. Next, referring to FIG. 6D, it illustrates the relationship diagram and a trend line of the concentrations of the proteins in the serum of the patient vs. the integral areas according to the results of FIG. 6C. It may be known from the results of FIG. 6D that a formula of the trend line is y=-0.1295x+2.6113, and a correlation coefficient ($R^2$) is 0.6308. In addition, it may be known from the results of FIG. 6C and FIG. 6D that the lowest detection limit of the protein sensor is $2.7\times10^{-5}$ μg/mL (i.e., $2.7\times10^{-2}$ ng/mL).

In addition, although the protein sensors of Embodiment 3 and Embodiment 4 take the detection of the ovarian cancer tumor marker CA125 as an example, the invention is not limited to this. That is, in some embodiments, the protein sensor of the invention may also be used to detect other proteins and peptides, such as tumor markers of prostate cancer, colorectal cancer, liver cancer or other cancers.

In addition, although the protein sensor is manufactured by using the hydrophobic material, the invention does not limit a source of the material of the protein sensor. Therefore, in some embodiments, graphene oxide may also be used to manufacture the protein sensor. Specifically, since the surface of the graphene oxide already has the hydrophilic functional group, there is no need to perform the atmospheric pressure plasma process on the graphene oxide. Therefore, the first antibody may be directly immobilized on the surface of graphene oxide. Then, after the graphene oxide is reacted with the antigen (such as the tumor marker CA125) and the second antibody, the protein sensor may be manufactured.

Based on the above, in the protein sensor and the manufacturing method thereof provided by the present embodiment, the hydrophilic functional group is formed on the surface of the hydrophobic material by using the atmospheric pressure plasma process, so that the first antibody may be immobilized on the surface of the hydrophobic material through the hydrophilic functional group. Then, the first antibody is used to identify and bind to the analyte that binds to the second antibody, so as to form the protein sensor of the present embodiment. Then, the detection is performed electrochemically. In this way, the protein sensor of the present embodiment may be used to identify types and quantities of proteins, and has a relatively low detection limit and relatively good sensitivity.

What is claimed is:

1. A manufacturing method of a protein sensor, comprising:
    providing a hydrophobic material, wherein the hydrophobic material comprises a surface;
    performing an atmospheric pressure plasma process to form a hydrophilic functional group on the surface of the hydrophobic material;
    immobilizing a first antibody on the surface of the hydrophobic material by the hydrophilic functional group;
    preparing a mixed solution, wherein the mixed solution comprises a second antibody and an analyte, and the second antibody binds to the analyte; and
    reacting the mixed solution with the first antibody immobilized on the surface of the hydrophobic material to bind the first antibody to the analyte,
    wherein the atmospheric pressure plasma process is a wet atmospheric pressure plasma modification method or a dry atmospheric pressure plasma modification method,
    wherein the wet atmospheric pressure plasma modification method comprises the following steps:
        dispersing the hydrophobic material in deionized water; and
        applying an atmospheric pressure plasma with a current of 10 mA to the surface of the hydrophobic material for 3 min,
    wherein the dry atmospheric pressure plasma modification method comprises the following step:
        applying an atmospheric pressure plasma with a power of 500 W and a frequency of 32 Hz to the surface of the hydrophobic material.

2. The manufacturing method of the protein sensor according to claim 1, wherein the hydrophobic material comprises graphite, graphene, or a gold sheet.

3. The manufacturing method of the protein sensor according to claim 1, wherein the hydrophilic functional group comprises a carboxyl group, a hydroxyl group, or a combination thereof.

4. The manufacturing method of the protein sensor according to claim 1, wherein the step of immobilizing the first antibody to the surface of the hydrophobic material by the hydrophilic functional group comprises: bonding an amino acid of the first antibody to the hydrophilic functional group on the surface of the hydrophobic material.

5. The manufacturing method of the protein sensor according to claim 1, wherein a source of the analyte comprises a cell extract or serum.

6. The manufacturing method of the protein sensor according to claim 1, wherein the analyte is a tumor marker CA125.

7. A protein sensor, manufactured by the manufacturing method of the protein sensor according to claim 1.

8. The protein sensor according to claim 7, wherein the protein sensor comprises a lowest detection limit of $2.7\times10^{-2}$ ng/mL to 3.2 ng/mL.

* * * * *